US008202699B2

(12) United States Patent
Hegemann et al.

(10) Patent No.: US 8,202,699 B2
(45) Date of Patent: *Jun. 19, 2012

(54) USE OF BIOLOGICAL PHOTORECEPTORS AS DIRECTLY LIGHT-ACTIVATED ION CHANNELS

(75) Inventors: Peter Hegemann, Falkensee (DE); Georg Nagel, Wuerzburg (DE); Ernst Bamberg, Kelkheim (DE)

(73) Assignee: Max-Planck-Gesellschaft Zur Forderung Der Wissenschaften E.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/781,962

(22) Filed: May 18, 2010

(65) Prior Publication Data

US 2011/0086421 A1    Apr. 14, 2011

Related U.S. Application Data

(63) Continuation of application No. 10/510,628, filed as application No. PCT/EP03/03799 on Apr. 11, 2003, now Pat. No. 7,824,869.

(30) Foreign Application Priority Data

Apr. 11, 2002    (DE) .................................. 102 16 005

(51) Int. Cl.
*G01N 33/00* (2006.01)
*C12N 5/07* (2010.01)
*C12N 5/10* (2006.01)
*C12N 1/19* (2006.01)
*C12N 5/0793* (2010.01)
*C12N 1/12* (2006.01)
*C12Q 1/02* (2006.01)

(52) U.S. Cl. ........ 435/7.21; 435/7.2; 435/325; 435/348; 435/352; 435/357; 435/358; 435/365; 435/368; 435/369; 435/372.1; 435/255.2; 435/255.5; 435/257.6; 435/375

(58) Field of Classification Search ........................ None
See application file for complete search history.

(56) References Cited

U.S. PATENT DOCUMENTS

| | | | |
|---|---|---|---|
| 4,879,284 | A | 11/1989 | Land et al. |
| 5,041,224 | A | 8/1991 | Ohyama et al. |
| 7,144,733 | B2 | 12/2006 | Miesenbock et al. |
| 2005/0202398 | A1 * | 9/2005 | Hegemann et al. ............... 435/4 |

FOREIGN PATENT DOCUMENTS

JP    06-295350    10/1994

OTHER PUBLICATIONS

Linsdell P et al. Non-pore lining amino acid side chains influence anion selectivity of the human CFTR Cl-channel expressed in mammalian cell lines. J Physiol. 1998; 512 (Pt. 1):1-16.*
Bieszke et al., Proc. Natl. Acad. Sci., 96, 8034-8039 (1999).
Hegemann, et al. Journal of Phycology, 37, 668-676 (2001).
Nagel et al., Science, 296, 2395-2398 (2002).
Perozo, et al., Biochemistry, 32, 10471-10478 (1993).
Sineshchekov, et al. Proc. natl. Acad. Sci., 99(13), 8689-8694 (2002).
Abdulaev NG and Ridge KD. Heterologous expression of bovine opsin in *Pichia pastoris*. Methods Enzymology, 2000; 315:3-11.
Han M, et al., Constitutive activation of opsin by mutation of methionine 257 on transmembrane helix 6. Biochemistry, 1998; 37: 8253-8261.
National Center for Biotechnology Information, "*Chlamydomonas reinhardtii* acop1 mRNA for archaeal-type opsin 1, complete cds.," "Accession No. AB058890 (Mar. 26, 2002) Accessed on the internet, Jan. 8, 2003).
National Center for Biotechnology Information, Blast sequence comparison of Accession No. AB058890.1 with SEQ ID No. 1 (Accessed on the internet, Jan. 8, 2003).
National Center for Biotechnology Information, "*Chlamydomonas reinhardtii* acop2 mRNA for archaeal-type opsin 2, complete cds.," "Accession No. AB058891 (Mar. 26, 2002) (Accessed on the internet, Jan. 8, 2003).
National Center for Biotechnology Information, Blast sequence comparison of Accession No. AB058891.1 with SEQ ID No. 2 (Accessed on the internet, Jan. 8, 2003).
Hildebrandt-K, et al., PNAS, 90(3578-3582)1993.
Muradin-Szweykowska, et al., Eur. J. Biochem, 140(1):176-176 (Apr. 2, 1984).
National Center for Biotechnology Information, "*Chlamydomonas reinhardtii* acop1 mRNA for archaeal-type opsin 1, complete cds.," "Accession No. AB058890 (Mar. 26, 2002) (Accessed on the internet, Jan. 8, 2003).

* cited by examiner

*Primary Examiner* — Elizabeth C Kemmerer
*Assistant Examiner* — Kimberly A Ballard
(74) *Attorney, Agent, or Firm* — Oblon, Spivak, McClelland, Maier & Neustadt, L.L.P.

(57) ABSTRACT

Use of a biological photoreceptor as light-controlled ion channel for the alteration of the ion conductivity of a membrane by means of light. The photoreceptor used comprises an apoprotein and a light-sensitive polyene covalently bound to the apoprotein, said polyene interacting with the apoprotein and functioning as a light-sensitive gate.

21 Claims, 11 Drawing Sheets

Figure 2:

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYAEWLLTCPVILIHLS
NLTGLANDYNKRTMGLLVSDIGTIVWGTTAALSKGYVRVIFFLMGLCYGIYTFFNAAKV
YIEAYHTVPKGICRDLVRYLAWLYFCSWAMFPVLFLLGPEGFGHINQFNSAIAHAILDL
ASKNAWSMMGHFLRVKIHEHILLYGDIRKKQKVNVAGQEMEVETMVHEEDDETQKV
PTAKYANRDSFIIMRDRLKEKGFETRASLDGDPNGDAEANAAAGGKPGMEMGKMTG
MGMGMGAGMGMATIDSGRVILAVPDISMVDFFREQFARLPVPYELVPALGAENTLQL
VQQAQSLGGCDFVLMHPEFLRDRSPTGLLPRLKMGGQRAAAFGWAAIGPMRDLIEG
SGVDGWLEGPSFGAGINQQALVALINRMQQAKKMGMMGGMGMGMGGGMGMGM
GMGMGMAPSMNAGMTGGMGGASMGGAVMGMGMGMQPMQQAMPAMSPMMTQ
QPSMMSQPSAMSAGGAMQAMGGVMPSPAPGGRVGTNPLFGSAPSPLSSQPGISP
GMATPPAATAAPAAGGSEAEMLQQLMSEINRLKNELGE

Fig. 1A

```
MDYGGALSAVGRELLFVTNPVVVNGSVLVPEDQCYCAGWIESRGTNGAQTASNVLQ
WLAAGFSILLLMFYAYQTWKSTCGWEEIYVCAIEMVKVILEFFFEFKNPSMLYLATGH
RVQWLRYAEWLLTCPVILIHLSNLTGLSNDYSRRTMGLLVSDIGTIVWGATSAMATGY
VKVIFFCLGLCYGANTFFHAAKAYIEGYHTVPKGRCRQVVTGMAWLFFVSWGMFPIL
FILGPEGFGVLSVYGSTVGHTIIDLMSKNCWGLLGHYLRVLIHEHILIHGDIRKTTKLNIG
GTEIEVETLVEDEAEAGAVNKGTGKYASRESFLVMRDKMKEKGIDVRASLDNSKEVE
QEQAARAAMMMMNGNGMGMGMGMNGMNGMGGMNGMAGGAKPGLELTPQLQP
GRVILAVPDISMVDFFREQFAQLSVTYELVPALGADNTLALVTQAQNLGGVDFVLIHP
EFLRDRSSTSILSRLRGAGQRVAAFGWAQLGPMRDLIESANLDGWLEGPSFGQGILP
AHIVALVAKMQQMRKMQQMQQIGMMTGGMNGMGGGMGGGMNGMGGGNGMNN
MGNGMGGGMGNGMGGNGMNGMGGGNGMNNMGGNGMAGNGMGGGMGGNGM
GGSMNGMSSGVVANVTPSAAGGMGGMMNGGMAAPQSPGMNGGRLGTNPLFNAA
PSPLSSQLGAEAGMGSMGGMGGMSGMGGMGGMGGMGGAGAATTQAAGGNAEA
EMLQNLMNEINRLKRELGE
```

Fig 1B

MlptavegvsqAQITGRPEWIWLALGTALMGLGTLYFLVKGMGVSDPDAKKFYAITTLVPAIAFT
MYLSMLLGYGLTMVPFGGEQNPIYWARYADWLFTTPLLLLDLALLVDADQGTILALVGADG
IMIGTGLVGALTKVYSYRFVWWAISTAAMLYILYVLFFGFTSKAESMRPEVASTFKVLRNVT
VVLWSAYPVVWLIGSEGAGIVPLNIETLLFMVLDVSAKVGFGLILLRSRAIFGEAEAPEPSAG
DGAAATSD

Fig. 1C

```
Chop1..MSRRPWLLALALAVALAAGSAGASTGSDATVPVATQDGPDYVFHRAHEAMAFQTSYTLEN  60
Chop2................................MDYGGALSAVGAEALFVTNPVVV  23
  Bop.............................................M

*                                          *
Chop1..NGSVICIPNNGQCFCLARLKSN--GTNAEKAANILMITFALAACANYGATNKSIC  118
Chop2..NGSVL-VAED-QCYCAGWIESR--GTNGAQTASAVAQWLAAHFAILAAYGAAKSIC   79
  Bop..LPTAVEGVSQAAITGRPEWIWLALATALMGAGTLYFLVKGMAVADPDAKKAYAIATLVPA  51

* *                        *  **    **    *
Chop1..GWEEAMATAEAIKFAIAYAHEADEAVIASSNANKTVNARYAEALTCEVALAHLSNLA  178
Chop2..GWEEAACAIAMVAKVIAFAFAAKNASMLALATAHRVQNAYAEALTCAVALAHLSALA  139
  Bop..IAFTMA---LSMLLGYGLTMVPAGGEQ-------APIYWARADALFITALLLDIA-AL  100

*     *              *      *         *    *
Chop1..GLANDYNKAW--GMAVSDLGALVWATTAAASKAVV-KVATFLMGACAGIKAAANAA-KVA  235
Chop2..GESNAASRAQA-GALAASDAGTANGASAMATGAV-KAIAECLAAGIAANTKAHAA-KAV  196
  Bop..V-DAA-Q-GAILAAVGAAGIMAGTALVGAAIKVASYRFVWWAISTAAMLAILYVLFFGFT  157

*                  *  **  *
Chop1..AAYATAVPKQICADLARYAAAYRCSAAMAAVAAAGAATAHINQFNAAIAAAAADAAS  295
Chop2..AAGYATAVPKQRCAQVATGMAALFAVSAGAAAIAAAQAQAALLSVYGATVGATAADMA  256
  Bop..SKAESMRAEV--ASTFKVARNVTVVLSAAAAVLAAIASAEAAAIVPLNIATLLFMVADVSA  215

Chop1..ANAAASMMGAFLRVKAIAAIALYADIRKQAVAVAQAMAVAMAHEADDETQKVP-AAKA  354
Chop2..ANCAGLLAHYAFULAHAAIAIHADIRAATTALNIGATAIAVATLAEDAAEAGAVNKGAGAA  316
  Bop..AVGAGLI--LAASRAIFGEAEAPEPSAGDGA-AATSD Chop1..ANAEDAAIIMAARLAEKAFETAAALAGDPNGDAAANAAAGGKPGMEMAKMTAAANSMGAA  414
Chop2..ASAEAALVAARDKMAEKAIDVAASAANSKEVEQAAQAAARAAMMMMNGNAMGMAMANGMNAA  376

Chop1..AMATIDS--------------ARVAIAVADIGAAADAFRAAFARIAPVAIAAVAPAAGAEAA  459
Chop2..AGMNGMAGGAKPGLELTPQLQPGAVALAVADIAMVAAARAAQAAQASVAVARAVAALGADNA  436

Chop1..AQAAAQAAGSAAGACAAVAMAPFLRAAAAPAGLAAPALKMGAAAAAAAAAAIAAMAADLATGS  519
Chop2..AAAATAAQAMAAGAVDAVAAIHAAALRDAASASSIAASAALRGAAQAVAAFGMAQLAAMAADLAAASA  496

Chop1..GVDAAAAAAGPSAGAAAANQQALVAAAINRAAGQAKKAMGMAG----------AMGMGAGAGG-A  568
Chop2..NLDAAAAAAAGPSAGAQAAALPAHIVAALVAKAAQAMRKAMQQAMQQIGMMTGGMNAGMAGGMAAANGM  556

Chop1..AMAAMAAAG-AAPSANAAGAMTGAAMAGA----ASMAGAA-----AVMAGAMAGAMGMQPAAQQAAAAP--AASPM  616
Chop2..AGGAANAAANNNMAGNGAMGGAAGNGAMAAGAMGMNGMAGGNGAMNMGAAAAAGNGAAGGGAAGGAGAGGS  616

Chop1..AATQQPA-MMSQPSAMSAAAAMQAAMAGVAAPSAAP----AAAVAATANAAAAAGSAAAAAAASA---  667
Chop2..ANGMSAGVVANVTPSAAAAGAMGGMAAAGMAAAAQS PGMNAAAALGTNAALANAAAPSALSGOLGA  676

Chop1..-----------------PAISPAAATPPAAAAPAAGSAAAAAMAQQLMSAAANAAN-AAOAK  712
Chop2..EAGMGSMGGMGGMSGMGGMAGMGAAGGAGAAAATQAAAGCNAAAAAAQNLMNAAANAAAARAAAAA  737
```

Fig. 1D

```
....5...10....5...20....5...30....5...40
MDYGGALSAVGRELLFVTNPVVNGSVLVPEDQCYCAGWI      40
ESRGTNGAQTASNVLQWLAAGFSILLLMFYAYQTWKSTCG     80
WEEIYVCAIEMVKVILEFFFEFKNPSMLYLATGHRVQWLR    120
YAEWLLTCPVILIRLSNLTGLSNDYSRRTMGLLVSDIGTI    160
VWGATSAMATGYVKVIFFCLGLCYGANTFFHAAKAYIEGY    200
HTVPKGRCRQVVTGMAWLFFVSWGMFPILFILGPEGFGVL    240
SVYGSTVGHTIIDLMSKNCWGLLGHYLRVLIHEHILIHGD    280
IRKTTKLNIGGTEIEVETLVEDEAEAGAVNKGTGK         315
```

Fig. 1E

SEQUENCE LISTING

<160> NUMBER OF SEQ ID NOS: 11

<210> SEQ ID NO 1
<211> LENGTH: 712
<212> TYPE: PRT
<213> ORGANISM: Chlamydomonas reinhardtii
<220> FEATURE:
<221> NAME/KEY: MISC_FEATURE
<222> LOCATION: (1)..(712)
<223> OTHER INFORMATION: Amino acid sequence of CHOP-1 from
      Chlamydomonas reinhardtii

<400> SEQUENCE: 1

```
Met Ser Arg Arg Pro Trp Leu Leu Ala Leu Ala Leu Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335
```

```
Thr Met Val His Glu Glu Asp Asp Glu Thr Gln Lys Val Pro Thr Ala
            340                 345                 350

Lys Tyr Ala Asn Arg Asp Ser Phe Ile Ile Met Arg Asp Arg Leu Lys
            355                 360                 365

Glu Lys Gly Phe Glu Thr Arg Ala Ser Leu Asp Gly Asp Pro Asn Gly
            370                 375                 380

Asp Ala Glu Ala Asn Ala Ala Gly Gly Lys Pro Gly Met Glu Met
385                 390                 395                 400

Gly Lys Met Thr Gly Met Gly Met Gly Ala Gly Met Gly Met
            405                 410                 415

Ala Thr Ile Asp Ser Gly Arg Val Ile Leu Ala Val Pro Asp Ile Ser
            420                 425                 430

Met Val Asp Phe Phe Arg Glu Gln Phe Ala Arg Leu Pro Val Pro Tyr
            435                 440                 445

Glu Leu Val Pro Ala Leu Gly Ala Glu Asn Thr Leu Gln Leu Val Gln
            450                 455                 460

Gln Ala Gln Ser Leu Gly Gly Cys Asp Phe Val Leu Met His Pro Glu
465                 470                 475                 480

Phe Leu Arg Asp Arg Ser Pro Thr Gly Leu Leu Pro Arg Leu Lys Met
            485                 490                 495

Gly Gly Gln Arg Ala Ala Ala Phe Gly Trp Ala Ala Ile Gly Pro Met
            500                 505                 510

Arg Asp Leu Ile Glu Gly Ser Gly Val Asp Gly Trp Leu Glu Gly Pro
            515                 520                 525

Ser Phe Gly Ala Gly Ile Asn Gln Gln Ala Leu Val Ala Leu Ile Asn
            530                 535                 540

Arg Met Gln Gln Ala Lys Lys Met Gly Met Met Gly Met Gly Met
545                 550                 555                 560

Gly Met Gly Gly Gly Met Gly Met Gly Met Gly Met Gly Met Gly Met
            565                 570                 575

Ala Pro Ser Met Asn Ala Gly Met Thr Gly Gly Met Gly Gly Ala Ser
            580                 585                 590

Met Gly Gly Ala Val Met Gly Met Gly Met Gly Met Gln Pro Met Gln
            595                 600                 605

Gln Ala Met Pro Ala Met Ser Pro Met Met Thr Gln Gln Pro Ser Met
            610                 615                 620

Met Ser Gln Pro Ser Ala Met Ser Ala Gly Gly Ala Met Gln Ala Met
625                 630                 635                 640

Gly Gly Val Met Pro Ser Pro Ala Pro Gly Gly Arg Val Gly Thr Asn
            645                 650                 655

Pro Leu Phe Gly Ser Ala Pro Ser Pro Leu Ser Ser Gln Pro Gly Ile
            660                 665                 670

Ser Pro Gly Met Ala Thr Pro Ala Ala Thr Ala Ala Pro Ala Ala
            675                 680                 685

Gly Gly Ser Glu Ala Glu Met Leu Gln Gln Leu Met Ser Glu Ile Asn
            690                 695                 700

Arg Leu Lys Asn Glu Leu Gly Glu
705                 710

<210> SEQ ID NO 2
<211> LENGTH: 737
<212> TYPE: PRT
<213> ORGANISM: Chlamydomonas reinhardtii
<220> FEATURE:
<221> NAME/KEY: MISC_FEATURE
<222> LOCATION: (1)..(737)
```

-continued

<223> OTHER INFORMATION: Amino acid sequence of CHOP-2 from
      Chlamydomonas reinhardtii
<220> FEATURE:
<221> NAME/KEY: MISC_FEATURE
<222> LOCATION: (2)..(737)
<223> OTHER INFORMATION: Amino acid sequence of CHOP-2 from
      Chlamydomonas reinhardtii

<400> SEQUENCE: 2

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                325                 330                 335

Arg Ala Ser Leu Asp Asn Ser Lys Glu Val Glu Gln Glu Gln Ala Ala
            340                 345                 350

Arg Ala Ala Met Met Met Met Asn Gly Asn Gly Met Gly Met Gly Met
        355                 360                 365

Gly Met Asn Gly Met Asn Gly Met Gly Gly Met Asn Gly Met Ala Gly

```
                370             375             380
Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
                405                 410                 415

Gln Phe Ala Gln Leu Ser Val Thr Tyr Glu Leu Val Pro Ala Leu Gly
            420                 425                 430

Ala Asp Asn Thr Leu Ala Leu Val Thr Gln Ala Gln Asn Leu Gly Gly
        435                 440                 445

Val Asp Phe Val Leu Ile His Pro Glu Phe Leu Arg Asp Arg Ser Ser
    450                 455                 460

Thr Ser Ile Leu Ser Arg Leu Arg Gly Ala Gly Gln Arg Val Ala Ala
465                 470                 475                 480

Phe Gly Trp Ala Gln Leu Gly Pro Met Arg Asp Leu Ile Glu Ser Ala
                485                 490                 495

Asn Leu Asp Gly Trp Leu Glu Gly Pro Ser Phe Gly Gly Ile Leu
            500                 505                 510

Pro Ala His Ile Val Ala Leu Val Ala Lys Met Gln Gln Met Arg Lys
        515                 520                 525

Met Gln Gln Met Gln Gln Ile Gly Met Met Thr Gly Met Asn Gly
    530                 535                 540

Met Gly Gly Gly Met Gly Gly Gly Met Asn Gly Met Gly Gly Asn
545                 550                 555                 560

Gly Met Asn Asn Met Gly Asn Gly Met Gly Gly Met Gly Asn Gly
                565                 570                 575

Met Gly Gly Asn Gly Met Asn Gly Met Gly Gly Asn Gly Met Asn
            580                 585                 590

Asn Met Gly Gly Asn Gly Met Ala Gly Asn Gly Met Gly Gly Met
        595                 600                 605

Gly Gly Asn Gly Met Gly Gly Ser Met Asn Gly Met Ser Ser Gly Val
    610                 615                 620

Val Ala Asn Val Thr Pro Ser Ala Ala Gly Met Gly Gly Met Met
625                 630                 635                 640

Asn Gly Gly Met Ala Ala Pro Gln Ser Pro Gly Met Asn Gly Gly Arg
                645                 650                 655

Leu Gly Thr Asn Pro Leu Phe Asn Ala Ala Pro Ser Pro Leu Ser Ser
            660                 665                 670

Gln Leu Gly Ala Glu Ala Gly Met Gly Ser Met Gly Gly Met Gly Gly
        675                 680                 685

Met Ser Gly Met Gly Gly Met Gly Gly Met Gly Gly Met Gly Gly Ala
    690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu

<210> SEQ ID NO 3
<211> LENGTH: 259
<212> TYPE: PRT
<213> ORGANISM: Halobacterium salinarum
<220> FEATURE:
<221> NAME/KEY: MISC_FEATURE
<222> LOCATION: (1)..(259)
<223> OTHER INFORMATION: Amino acid sequence of bacteriorhodopsin from
      Halobacterium salinarum
```

<400> SEQUENCE: 3

```
Met Leu Pro Thr Ala Val Glu Gly Val Ser Gln Ala Gln Ile Thr Gly
1               5                   10                  15

Arg Pro Glu Trp Ile Trp Leu Ala Leu Gly Thr Ala Leu Met Gly Leu
            20                  25                  30

Gly Thr Leu Tyr Phe Leu Val Lys Gly Met Gly Val Ser Asp Pro Asp
        35                  40                  45

Ala Lys Lys Phe Tyr Ala Ile Thr Thr Leu Val Pro Ala Ile Ala Phe
    50                  55                  60

Thr Met Tyr Leu Ser Met Leu Leu Gly Tyr Gly Leu Thr Met Val Pro
65                  70                  75                  80

Phe Gly Gly Glu Gln Asn Pro Ile Tyr Trp Ala Arg Tyr Ala Asp Trp
                85                  90                  95

Leu Phe Thr Thr Pro Leu Leu Leu Asp Leu Ala Leu Leu Val Asp
            100                 105                 110

Ala Asp Gln Gly Thr Ile Leu Ala Leu Val Gly Ala Asp Gly Ile Met
        115                 120                 125

Ile Gly Thr Gly Leu Val Gly Ala Leu Thr Lys Val Tyr Ser Tyr Arg
    130                 135                 140

Phe Val Trp Trp Ala Ile Ser Thr Ala Ala Met Leu Tyr Ile Leu Tyr
145                 150                 155                 160

Val Leu Phe Phe Gly Phe Thr Ser Lys Ala Glu Ser Met Arg Pro Glu
                165                 170                 175

Val Ala Ser Thr Phe Lys Val Leu Arg Asn Val Thr Val Val Leu Trp
            180                 185                 190

Ser Ala Tyr Pro Val Val Trp Leu Ile Gly Ser Glu Gly Ala Gly Ile
        195                 200                 205

Val Pro Leu Asn Ile Glu Thr Leu Leu Phe Met Val Leu Asp Val Ser
    210                 215                 220

Ala Lys Val Gly Phe Gly Leu Ile Leu Leu Arg Ser Arg Ala Ile Phe
225                 230                 235                 240

Gly Glu Ala Glu Ala Pro Glu Pro Ser Ala Gly Asp Gly Ala Ala Ala
                245                 250                 255

Thr Ser Asp
```

<210> SEQ ID NO 4
<211> LENGTH: 315
<212> TYPE: PRT
<213> ORGANISM: Chlamydomonas reinhardtii
<220> FEATURE:
<221> NAME/KEY: MISC_FEATURE
<222> LOCATION: (1)..(315)
<223> OTHER INFORMATION: Amino acid sequence of the CHOP2-315/H134R mutant

<400> SEQUENCE: 4

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80
```

```
Trp Glu Glu Ile Tyr Val Cys Ala Ile Glu Met Val Lys Val Ile Leu
             85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile Arg Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
            165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Asn Lys Gly Thr Gly Lys
305                 310                 315

<210> SEQ ID NO 5
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: "Xaa" may be Leu or Ile
<220> FEATURE:
<221> NAME/KEY: MISC_FEATURE
<222> LOCATION: (3)..(8)
<223> OTHER INFORMATION: "x" is any amino acid
<220> FEATURE:
<221> NAME/KEY: MISC_FEATURE
<222> LOCATION: (3)..(5)
<223> OTHER INFORMATION: "Xaa" may be any amino acid
<220> FEATURE:
<221> NAME/KEY: MISC_FEATURE
<222> LOCATION: (7)..(8)
<223> OTHER INFORMATION: "Xaa" may be any amino acid
<220> FEATURE:
<221> NAME/KEY: MISC_FEATURE
<222> LOCATION: (9)..(9)
<223> OTHER INFORMATION: "Xaa" may be Trp, Phe, or Tyr

<400> SEQUENCE: 5

Xaa Asp Xaa Xaa Xaa Lys Xaa Xaa Xaa
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(8)
<223> OTHER INFORMATION: "x" is any amino acid

<400> SEQUENCE: 6

Leu Asp Xaa Xaa Xaa Lys Xaa Xaa Trp
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(8)
<223> OTHER INFORMATION: "x" is any amino acid

<400> SEQUENCE: 7

Ile Asp Xaa Xaa Xaa Lys Xaa Xaa Trp
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(8)
<223> OTHER INFORMATION: "x" is any amino acid

<400> SEQUENCE: 8

Leu Asp Xaa Xaa Xaa Lys Xaa Xaa Phe
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(8)
<223> OTHER INFORMATION: "x" is any amino acid

<400> SEQUENCE: 9

Leu Asp Xaa Xaa Xaa Lys Xaa Xaa Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(8)
<223> OTHER INFORMATION: "x" is any amino acid

<400> SEQUENCE: 10
```

```
Ile Asp Xaa Xaa Xaa Lys Xaa Xaa Phe
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(8)
<223> OTHER INFORMATION: "x" is any amino acid

<400> SEQUENCE: 11

Ile Asp Xaa Xaa Xaa Lys Xaa Xaa Tyr
1               5
```

USE OF BIOLOGICAL PHOTORECEPTORS AS DIRECTLY LIGHT-ACTIVATED ION CHANNELS

CROSS-REFERENCE TO RELATED APPLICATIONS

This application is a continuation of U.S. Ser. No. 10/510,628 filed May 9, 2005, now U.S. Pat. No. 7,824,869, which is a 371 of PCT/EP03/03799 filed Apr. 11, 2003 and claims the benefit of DE 102 16 005.8 filed Apr. 11, 2002.

The present invention concerns the use of biological photoreceptors as directly light-controlled ion channels.

It has been known for some time that a large number of central processes in plant and animal cells are wholly or partially controlled via changes in the intracellular concentrations of certain ions, for example the proton concentration, and changes in the membrane potential and the ion gradients across the membrane. Accordingly, the elucidation of mechanisms of intracellular ion regulation, in particular pH regulation, and the mechanisms of voltage-dependent ion channels and ion transporters are the subject of extensive research activities. For such research, a rapid and simple measurement and/or manipulation of intracellular ion concentrations, in particular proton concentrations, and of electrical gradients and ion gradients, in particular proton gradients, across cell membranes is of great interest.

A basically very advantageous approach to making such measurements and/or manipulations possible would be the introduction of a light-controlled ion channel into such a membrane, in order to alter deliberately the membrane potential and/or the flow of certain ions, e.g. protons, through the membrane.

In the state of the art, a number of light-controlled ion transport systems are known. At the same time, a distinction is made between passive and active ion transport systems. In the passive ion transport systems, the actual transport molecules, the so-called ion channels, are in interaction with separate photoreceptor complexes and are controlled indirectly via these photoreceptors. Examples of such photoreceptor complexes interacting with an ion channel are the G-protein activating rhodopsins; see for example Müller, F., Kaupp, U. B., Signaltransduktion in Sehzellen, Naturwissenschaften 85 (1998) 49-61. Since these known passive ion transport systems require the combined action of several proteins and other components, there are problems in introducing them into other cells with the retention of their function, e.g. by co-expression of the relevant proteins in recombinant systems. Examples of light-controlled active ion transport molecules in a cell membrane are the rhodopsins from archaea (archaebacteria). A known example of an archaeal rhodopsin is bacteriorhodopsin, consisting of a protein component, bacterioopsin, and a retinal linked via a Schiff's base. After excitation by light of suitable wavelength, bacteriorhodopsin transports protons through the membrane from the cell interior to the outside. As a rule, the ion transport proceeds slowly ($<100$ H$^+$/second) and the transport direction of the bacteriorhodopsin cannot be freely specified. In vivo, bacteriorhodopsin transports protons even against an existing electrochemical gradient, which is composed of a pH gradient and an electrical gradient $\Delta\Psi$. Such a light-controlled proton pump is a comparatively simple system. Bacteriorhodopsin and related retinal-binding proteins such as the chloride pump halorhodopsin have already been expressed heterologously and were capable of the light-driven active membrane transport of ions, e.g. H$^+$ or Cl$^-$, in the heterogeneous host.

However, for many purposes the known systems are unsuitable on account of their complexity or the predetermined transport direction.

One purpose of the present invention is to provide ways and means that allow rapid and simple measurement and/or manipulation of intracellular ion concentrations, in particular proton concentrations, and of electrical gradients across a cell membrane.

A further purpose is to provide a system which is suitable for the high throughput screening of biological molecules, in particular of pH-regulating membrane proteins and voltage-dependent membrane proteins.

The present invention solves these problems through the use of a new class of photoreceptors of previously unknown function, which are directly light-controlled passive ion transport systems (a light-controlled ion channel). This photoreceptor comprises an apoprotein which mediates ion conductivity, and a light-sensitive polyene covalently bound to the apoprotein, which interacts with the apoprotein and functions as a light-sensitive gate. Surprisingly, it has been possible according to the invention to combine the advantages of a relatively simple directly light-controlled system with the advantages of a passive ion channel.

The apoprotein is a membrane protein with at least 5 transmembrane helices, which is capable of binding a light-sensitive polyene. Transmembrane proteins with 6 or 7 transmembrane helices are preferable. Transmembrane proteins with more than 7 helices, for example 8, 9 or 10 transmembrane helices, are however also covered by the invention. Furthermore, the invention covers transmembrane proteins which in addition to the transmembrane part include C- and/or N-terminal sequences, where the C-terminal sequences can extend into the inside of the lumen enclosed by the membrane, for example the cytoplasm of a cell or the inside of a liposome, or can also be arranged on the membrane outer surface. The same applies for the optionally present N-terminal sequences, which can likewise be arranged both within the lumen and also on the outer surface of the membrane. The length of the C- and/or N-terminal sequences is in principle subject to no restriction; however, apoproteins with C-terminal sequences not embedded in the membrane, with 1 to 1000 amino acids, preferably 1 to 500, especially preferably 5 to 50 amino acids, are preferred. Independently of the length of the C-terminal sequences, the N-terminal located sequences not embedded in the membrane preferably comprise 1 to 500 amino acids, especially preferably 5 to 50 amino acids.

The concept of the transmembrane helix is well known to the skilled person. These are generally α-helical protein structures, which as a rule comprise 20 to 25 amino acids. However, depending on the nature of the membrane, which can be a natural membrane, for example a cell or plasma membrane, or also a synthetic membrane, the transmembrane segments can also be shorter or longer. For example, transmembrane segments in artificial membranes can comprise up to 30 amino acids, but on the other hand also only a few amino acids, for example 12 to 16.

The ion channel according to the invention can in principle serve for the passive transport of all physiologically important ions. The best known ion transport systems transport Na$^+$, K$^+$, Ca$^{2+}$, H$^+$ or Cl$^-$. In a preferred embodiment, the ion channel according to the invention is a proton channel.

In an especially preferred embodiment, the proton channel includes an opsin protein or a derivative or fragment of a naturally occurring opsin protein as the apoprotein portion. Here, opsins refers to apoproteins which are covalently bound to a retinoid chromophore and display ion conductivity as soon as they absorb light. A molecule which contains a retinoid chromophore covalently bound to an opsin is referred to as rhodopsin.

A derivative of an opsin molecule which occurs naturally and functions as a light-switched ion channel is altered compared to the original by an exchange of one or several amino acids, by an insertion and/or deletion of one or several amino acids at one or several positions. Both the naturally occurring opsin molecules and also their derivatives should display an identity of at least 15% with the sequence of the bacteriorhodopsin in the region of the 5 transmembrane helices which correspond to the helices 3 to 7 in the bacteriorhodopsin. An identity of 20% or more between the derivatives of a channel opsin and bacteriorhodopsin, based only on the region of the helices 3 to 7 in bacteriorhodopsin, is however preferred. On the other hand, the identity in the regions of the opsin derivative which do not correspond to the helices 3 to 7 can be far lower.

The term "identity" here refers to the degree of relatedness between two or more protein sequences, which is determined by the match between these sequences. The percentage is obtained as the percentage of identical amino acids in two or more sequences taking account of gaps and other sequence features.

The identity of mutually related protein molecules can be determined by means of known procedures. As a rule, special computer programmes with algorithms taking account of the particular requirements are used. Preferred procedures for the determination of the identity first generate the greatest match between the sequences under investigation. Computer programmes for the determination of the identity between two sequences include, but are not restricted to, the GCG programme package, including GAP (Devereux et al., 1984); Genetics Computer Group University of Wisconsin, Madison, (WI)); BLASTP, BLASTN and FASTA (Altschul et al., NCB NLM NIH Bethesda Md. 20894; Altschul et al., 1990). The well-known Smith Waterman algorithm can also be used for the determination of identity.

Preferred parameters for the sequence comparison include the following:
Algorithm: Altschul et al., 1990 (Basic local alignment search tool, J. Mol. Biol. 215, 403-410) (=BLAST)
Comparison matrix: BLOSUM 62 (Henikoff and Henikoff, 1992, Amino acid substitutions from protein blocks. PNAS 89, 10915-10919)
Agreement (matches)=variable
Non-agreement (mismatch)=variable
Gap value: open 10
Gap length value (gap length penalty): 1

The GAP programme is also suitable for use with the above parameters. The above parameters are the standard parameters (default parameters) for protein comparisons.

Further examples of algorithms, gap opening values (gap opening penalties), gap extension values (gap extension penalties), and comparison matrices including those mentioned in the programme handbook, Wisconsin Package, Version 9, September 1997, can be used. The choice will depend on the comparison to be performed and also on whether the comparison is performed between sequence pairs, in which case GAP or Best Fit are preferred, or between a sequence and an extensive sequence database, in which case FASTA or BLAST are preferred.

For the active proton pump bacteriorhodopsin, it is known that $Asp(D)^{96}$ is an amino acid essential for the proton pump function. Further, the following 16 amino acids of the bacteriorhodopsin are involved in the proton network:
$F^{42}, T^{46}, Y^{57}, R^{82}, D^{85}, T^{89}, L^{93}, T^{107}, W^{182}, Y^{185}, W^{189}, E^{194}, E^{204}, D^{212}, K^{216}, F^{219}$ In the ion channel according to the invention, a different amino acid from "D" is at the position corresponding to the $D^{96}$ of the bacteriorhodopsin sequence. $E^{204}$ is preferably replaced by S. In one embodiment, however, at least 8 of the other 15 amino acids are retained identical or only altered by conservative exchange. The amino acids which should as far as possible be retained identical are preferably $T^{46}, Y^{57}, R^{82}, T^{89}, T^{107}, W^{182}, E^{194}, D^{212}$, and $K^{216}$. Conservatively exchanged amino acids are preferably $F^{42}, D^{85}, L^{93}, Y^{185}, W^{189}$, and $F^{219}$. The skilled person knows here that for a conservative exchange an amino acid is selected which is functionally similar to the amino acid to be exchanged. Thus exchanges are normally effected within the following groups:

| (a) | Ala (A) | Ser (S) | Thr (T) | Pro (P) | Gly (G); |
|-----|---------|---------|---------|---------|---------|
| (b) | Asn (N) | Asp (D) | Glu (E) | Gln (Q); | |
| (c) | His (H) | Arg (R) | Lys (K) | | |
| (d) | Met (M) | Leu (L) | Ile (I) | Val (V) | and |
| (e) | Phe (F) | Tyr (Y) | Trp (W). | | |

Based on the amino acids stated above, preferred exchanges are the following: F42Y, D85E, Y185F, W189F, and F219W.

In a further preferred embodiment, one or several more of the following positions, based on bacteriorhodopsin, are contained in the ion channel according to the invention: $Y^{83}, W^{86}, P^{91}, G^{122}, P^{186}$ and $G^{195}$.

In a further preferred embodiment, a passive proton channel according to the invention contains an apoprotein with the consensus sequence L(I)DxxxKxxW(F,Y) (SEQ ID NO: 5). Amino acids given in brackets can in each case replace the preceding amino acid (e.g. LDxxxKxxW (SEQ ID NO: 6), IDxxxKxxW (SEQ ID NO: 7). LDxxxKxxF (SEQ ID NO: 8). LDxxxKxxY (SEQ ID NO: 9), IDxxxKxxF (SEQ ID NO: 10), and IDxxxKxxY (SEQ ID NO: 11)). This consensus sequence is the motif surrounding the retinal-binding amino acid lysine. In bacteriorhodopsin, the "K" at position 6 of the consensus sequence corresponds to K216 in the 7th helix of the bacteriorhodopsin.

In a preferred embodiment, the ion channel includes an apoprotein from lower eukaryotes. The group of the lower eukaryotes includes for example algae, protozoa, ciliates and yeasts.

Especially preferred here are motile green algae, in particular Chlorophyceae. Apoproteins from Volvocales are of particular interest here. In the most preferred embodiment, the apoprotein is an opsin protein from *Chlamydomonas reinhardtii*. Further green algae with preferred embodiments can be found among the Ulvophytes such as *Acetabularia* and *Ulva*. Further preferred embodiments are opsins from Prasinophyceae, for example *Pyramimonas* and *Platymonas* (*Tetraselmis*). Other preferred forms derive from the kingdom of the Dinophytes with the individual class of the Dinophyceae and for example the members *Gymnodinium splendens, Gyrodinium dorsum, Peridinium balticum* and *Gonyaulax*.

In a further preferred embodiment, the opsin functioning as a light-controlled ion channel is derived from a protozoon, a bacterium or an archaebacterium.

In a further preferred embodiment, the opsin functioning as a light-controlled ion channel is derived from fungi such as *Neurospora crassa, Fusarium sporotrichioides* and *Lep-* tosphaeria maculans, or Chytridiomyceten such as for example Allomyces reticulatus, or from ciliates such as Fabrea salina or Paramecium bursaria or from Foraminifera such as Amphistegina radiata.

According to the invention, two different proteins of known sequence were functionally expressed from Chlamydomonas reinhardtii and for the first time identified as passive ion transport systems. These are Channelopsin1 (=CHOP-1; also called Chlamyopsin-3=COP3) and Channelopsin2 (=CHOP-2; also called Chlamyopsin-4=COP4).

The CHOP-1 protein has a molecular weight of 76 kD and a length of 712 amino acids. It was identified on the basis of overlapping partial cDNA sequences in a C. reinhardtii EST database (Asamizu et al., DNA Research 7, 305-7 (2000)). Its amino acid sequence is shown in FIG. 1 of the present application. The core protein (amino acids 76-309) includes 7 hypothetical transmembrane segments with 15-20% homology to the sensory archaeal rhodopsins, the ion transporters bacteriorhodopsin (BR) and halorhodopsin (FIR), and to an only recently identified rhodopsin from the fungus Neurospora crassa (NOP1). Quantitatively, these homology levels are admittedly relatively low, however, on comparison with BR, those amino acids which define the retinal binding site and the W transport network in BR are specifically conserved. The consensus motif LDxxxKxxW (SEQ ID NO: 6) observed suggests that in CHOP-1 $K^{296}$ is the retinal-binding amino acid. 9 out of 22 amino acids which are in direct contact with the retinal in bacteriorhodopsin are identically retained in CHOP-1 and 4 others reflect only conservative changes ((FIG. 1); Nagel et al, in preparation).

Detailed studies of the light-controlled ion transport function of the CHOP-1 protein in oocytes from Xenopus laevis showed that the transported ions are protons (FIG. 3), and moreover that the ion transport is of a purely passive nature (FIG. 4a-c). The induced photocurrent and hence the ion transport is dependent on the wavelength of the excitant light and reaches a maximum at 500 nm (FIG. 4d).

Analogous experiments with two shorter fragments of the CHOP-1 protein, which included the amino acids 1-346 and 1-517 respectively, yielded results which were essentially identical with those for the full-length CHOP-1 protein. This demonstrates that a large part of the carboxy terminal region of the CHOP-1 protein is not necessary for the ion transport function.

The CHOP-1 protein from C. reinhardtii is the first identified example of a new directly light-controlled passive ion transport protein. Structurally and/or functionally similar rhodopsin proteins also occur in other microalgae and in gametes and zoospores of macroalgae and possibly also in other organisms.

The second protein identified as an apoprotein of a light-switched ion channel is Channelopsin2 (CHOP-2), whose sequence comprising 737 amino acids is also shown in FIG. 1. It displays a homology of 52.7% to CHOP-1. The amino acids important for transport identified via the homology between BR and CHOP-1 and model calculations are also largely conserved in CHOP-2. For this rhodopsin also, a light-switched passive proton conductivity was for the first time demonstrated by expression in Xenopus oocytes. The ion channel formed with CHOP-2 as apoprotein differs from that formed with CHOP-1 in terms of its unit conductivity, its inactivation under prolonged illumination and the shape of the current-voltage curve. Channelrhodopsin-2 (ChR2), which is made up of the protein Channelopsin-2 (CHOP-2) and retinal, is a light-controlled cation channel, which is permeable for example to $Li^+$, $Na^+$, $K^+$, $Ba^{2+}$, $Sr^+$ and $Ca^{2+}$, but not to $Mg^{2+}$. The maximum for the excitant light lies at 440-480 nm.

Figure 5:
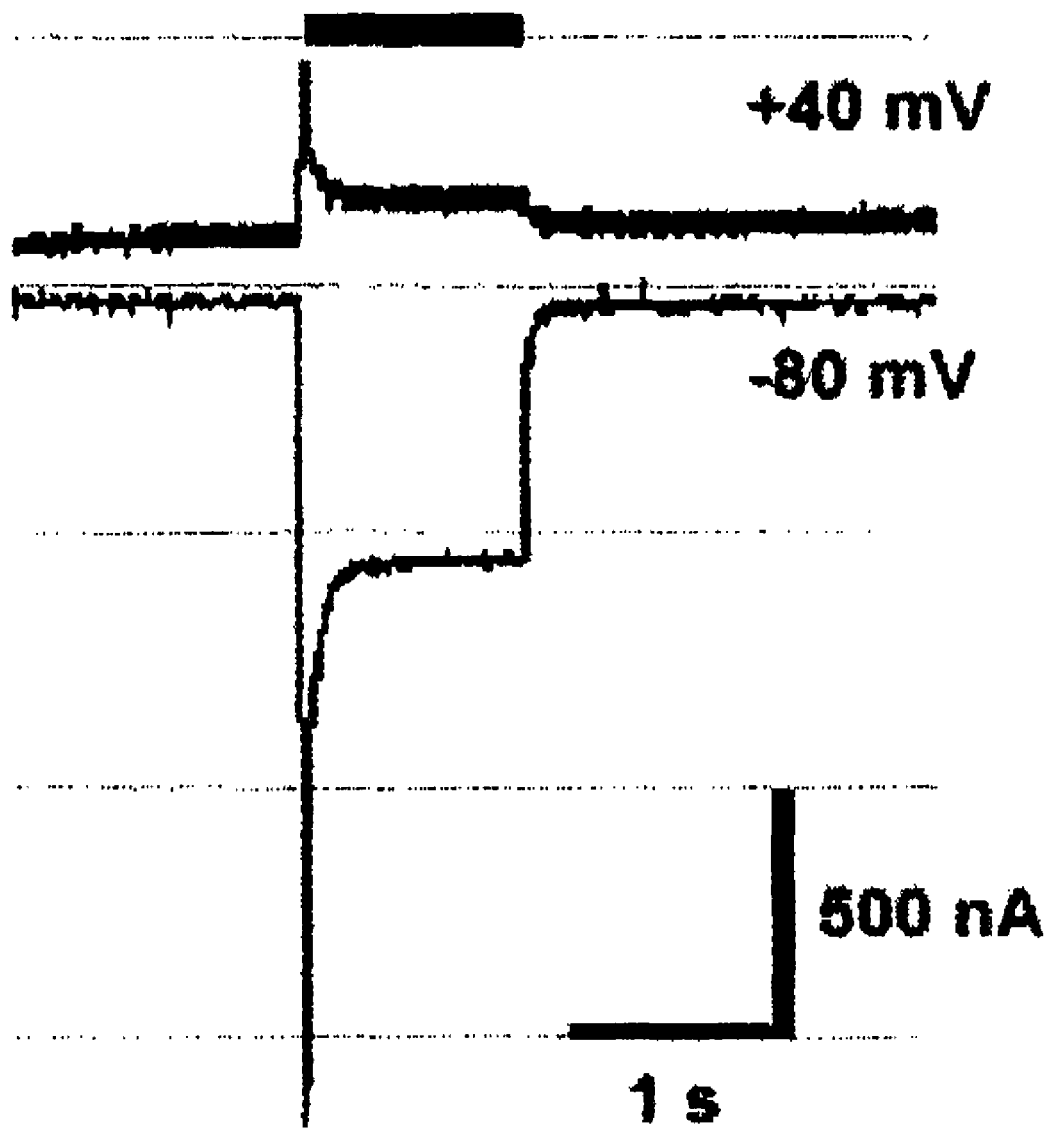
Figure 6:
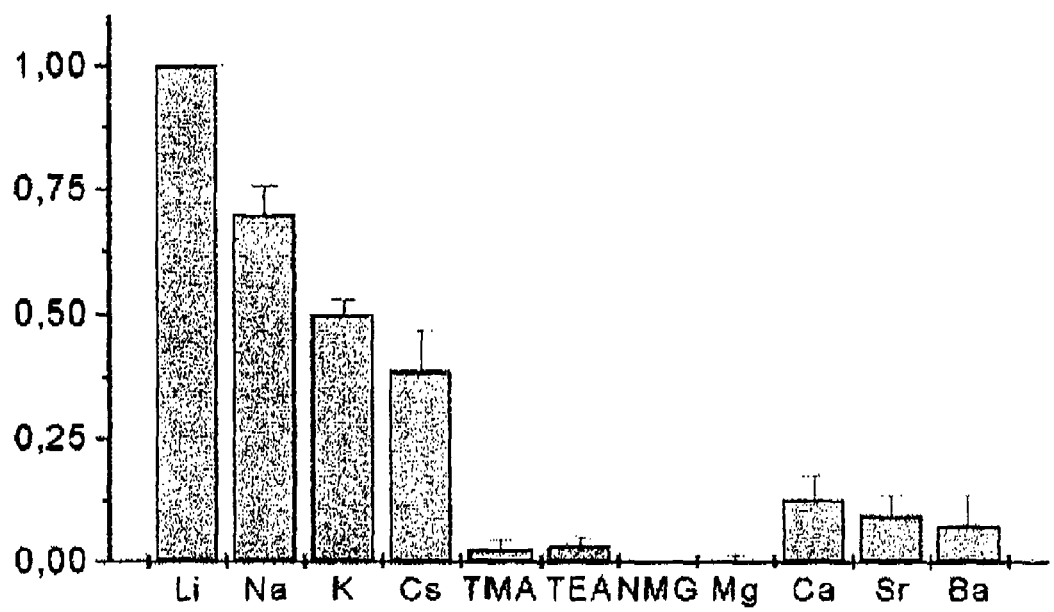
Figure 7:
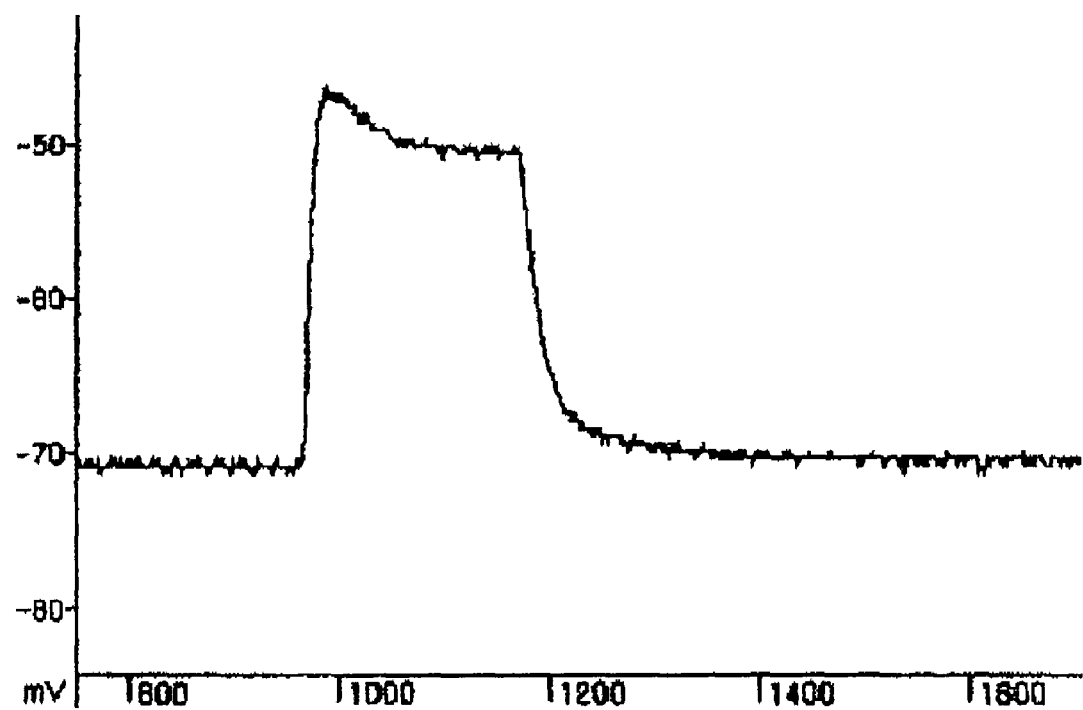

Similarly to the case of the CHOP-1 protein, it could also be shown here that a shortened form of CHOP-2 which contains the amino acids 1-315 likewise forms a functional light-switched ion channel (FIGS. 5-7).

CHOP-2 and or CHOP-2-315 can be used for the depolarisation of cells (see FIG. 7) or for $Ca^{2+}$ uptake (FIG. 6) or for both.

In the context of the present invention, with knowledge of the nucleotide and amino acid sequence and the calculated 3D structure of the natural CHOP-1 and CHOP-2 protein the skilled person is capable of preparing derivatives of the original amino acid sequence by exchange and/or insertion and/or deletion of one or several amino acid(s), which have wholly or partially retained the ion transport properties of the original protein or differ significantly with regard to ion specificity, inactivation, alignment, etc. Derivatives here are defined as stated above.

Active ion transport systems can be clearly and unequivocally distinguished electrophysiologically from passive systems as described below. In the light, passive light-controlled ion channels, which are an object of the invention, increase the conductivity of membranes into which they are incorporated, compared to the dark state. The ion currents which arise on illumination (photocurrents) are carried by the ion species which are conducted by the light-controlled ion channel. With equal concentration of the ions conducted (for CHOP-1 protons; for CHOP-2 for example protons) on both sides of the membrane (symmetrical conditions), the direction of the photocurrent is determined solely by the applied membrane potential. In the case of a positive charge carrier, with a negative potential (negative in the cell), an inward current takes place with movement of the positively charged ions into the cell, and with a positive potential (positive within) an outward current with movement of the positively charged ions out from the cell. With a symmetrical distribution of the transported ions, the current-voltage curves of a light-controlled ion channel according to the invention always pass through the origin (reversal potential $E_H=0$). However, the current-voltage curves of the light-controlled ion channels according to the invention are not necessarily linear. In the preferred embodiment of CHOP-1 for example, the current is conducted better in the inward direction than in the outward direction (inward rectifier, see FIGS. 2 and 3).

In contrast to this, in all active transport systems (such as for example bacteriorhodopsin), with symmetrical ion distribution the current-voltage curve never passes through the origin. The establishment of an unequal distribution of the conducted ions between inside and outside results in a displacement of the current-voltage curves along the voltage scale in accordance with the Nernst equation, i.e. by 58 mV for monovalent ions and by 29 mV for divalent ions.

Hence by investigation of the current-voltage curves it is possible to establish for every light-controlled ion channel whether it is a passive or an active system.

The present invention thus also concerns derivatives and fragments of the CHOP proteins which have wholly or partially retained the ion transport properties of the original protein or even display them to an increased extent, and structurally and functionally similar opsins from other organisms, of natural origin or modified by the use of recombinant techniques, if they display the stated biophysical properties and like CHOP-1 and CHOP-2 can be used for the stated purposes.

Extensive ranges of experiments for the preparation and study of such derivatives led to the surprising result that the amino acid position 134 in the CHOP-2 protein is of particular importance for the function as light-switched ion channel. Thus for example, by exchange of histidine at position 134 for arginine a particularly active mutant of the complete CHOP-2 protein or of the shortened CHOP-2-315 protein can be created. This exchange can be performed by standard procedures, for example by site-directed oligonucleotide mutagenesis. Further data suggest that Glu123 is involved in, a light-induced deprotonation, which leads to a desensitisation of the ion channel. Thus the mutation of Glu123 to Asp (E123D) markedly increased the ratio of the transient photocurrent to the equilibrium photocurrent, while the mutation of Glu123 to Gln (E123Q) causes the peak of the transient photocurrent almost to disappear, but also leads to a marked diminution in the steady-state photocurrent.

The passive ion transport system according to the invention contains a light-sensitive polyene. This can for example be p-hydroxycinnamic acid, retinal or a retinal derivative. Preferred retinal derivatives are selected from the following group: 3,4-dehydroretinal, 13-ethylretinal, 9-dm-retinal, 3-hydroxyretinal, 4-hydroxyretinal, naphthylretinal; 3,7,11-trimethyl-dodeca-2,4,6,8,10-pentaenal; 3,7-Dimethyl-deca-2,4,6,8-tetraenal; 3,7-Dimethyl-octa-2,4,6-trienal; and 6-7, or 10-11 rotation-blocked retinals with 4-, 5-, 6- or 7-member ring bridges. Especially preferred, however, is a 10-12-five-member ring-bridged retinal (Takahashi et al. FEBS Lett. 314, 275-279).

After light absorption and isomerisation of the polyenes, a structural alteration in the protein (opsin) takes place in the light-controlled ion channels according to the invention, and hence the opening of the ion-conducting channel, which links the intracellular with the extracellular side of the membrane. This event differs fundamentally from the situation in the known ion pumps, in which the extracellular proton-conducting half-channel (EC) is never conductively connected to the intracellular half-channel (IC). In bacteriorhodopsin, the Schiff's base of retinal is conductively connected to the extracellular side in the early M intermediate of the reaction cycle (photocycles), and conversely in the late M state it is connected to the intracellular side.

The light-controlled ion channels according to the invention can be incorporated into a membrane, for example the plasma membrane of a cell, and used to alter the membrane potential rapidly and in a defined manner through illumination, which is very helpful for the elucidation of the mechanisms of voltage-dependent ion channels or ion transporters. Further, the possibility thus arises of altering the intracellular levels of these ions rapidly and in a defined manner by targeted light-controlled ion transport.

In the case of the CHOP-1 protein, this means a targeted, non-invasive alteration of the intracellular pH value, which is of use for the elucidation of the mechanisms of intracellular pH regulation or the influence of transient pH changes on endogenous cell proteins.

With knowledge of the extracellular pH, the intracellular pH directly under the membrane or a pH gradient across the membrane can be rapidly and accurately measured through the measurement of the reversal potential of the light-induced CHOP-1 mediated proton conductivity. For this, the reversal potential is determined with the "Voltage Clamp" measurement used in FIGS. 2-4, and the cells are thus calibrated. After this, the modulation of the membrane potential and/or the intracellular pH be effected non-invasively with light via the light-controlled ion channel according to the invention. The relevant measurements are performed rapidly and in a defined manner and are thus ideally suitable for modern HTS (High-Throughput-Screening) instruments, with which for example pH-regulated voltage-dependent membrane proteins such as ion channels can be tested in screening applications with high throughput. Abrupt changes in potential or pH can be induced with light in cell lines which contain ChR1 or related rhodopsins.

An especially interesting application is optoelectrical coupling by light-controlled modulation of the membrane potential. This application is based on a combination of the light-controlled passive ion channel with a light-controlled active ion transport system, e.g. an ion pump, wherein, a different wavelength is preferably used for the light-control of the passive ion channel than for the light-control of the active ion transport system. In a preferred embodiment, light of a wavelength of 650 nm is used for the activation of the proton pump bacteriorhodopsin and for building up a membrane potential and then light of a wavelength of 440 nm, which has an inhibitory action on bacteriorhodopsin, is used for the activation of the CHOP-1 proton transport system and for rapid dissipation of the potential.

Light-regulated ion channels can also be used in signal transfer from neuronal networks to microelectrode networks. In this way, transfer of electrical impulses from neurones to microcomputers is being attempted ("Interfacing of Nerve Cells and Semiconductors": Fromherz (2001), Physikalische Blätter 57, 43-48). Hitherto, the neurones had to be stimulated either via neurotransmitters or directly with micropipettes. Neurones which express ChR1, ChR2 or related light-controlled ion channels could be controlled with light.

A further application is the treatment of blind animals or in the final analysis people. There are a number of diseases in which the natural visual cells no longer function, but all nerve connections are capable of continuing to operate. Today, attempts are being made in various research centres to implant thin films with artificial ceramic photocells on the retina (E. Zrenner (2002) Science 295, 1022-1025.) These photocells are intended to depolarise the secondary, still intact cells of the retina and thereby to trigger a nerve impulse (bionic eyes). The deliberate expression of light-controlled rhodopsins such as ChR1 or ChR2 in these ganglion cells, amacrine cells or bipolar cells would be a very much more elegant solution and enable greater three-dimensional visual resolution.

The incorporation of the rhodopsin ion transport system according to the invention into the membrane of cells which do not express the corresponding opsin protein in nature can for example be simply effected in that, using known procedures of recombinant DNA technology, the DNA coding for this opsin is firstly incorporated into a suitable expression vector, e.g. a plasmid, a cosmid or a virus, the target cells are then transformed with this, and the protein is expressed in this host. Next, the cells are treated in a suitable manner, e.g. with retinal, in order to enable the linkage of a Schiff's base between protein and retinal.

In a preferred embodiment, this occurs in various yeasts such as *Saccharomyces cerevisiae, Schizosaccharomyces pombe* or *Pichia pastoris* as already successfully performed for rhodopsins such as bacteriorhodopsin and/or bovine rhodopsin (Hildebrandt V. et al. (1989)), Genetic transfer of the pigment bacteriorhodopsin into the eukaryote *Schizosaccharomyces pombe*, FEBS Lett. 243(2):137-40; Najmoutin G. et al., Heterologous expression of bovine opsins in *Pichia pastoris, Meth. Enzymol.* (2000) 315, 3-11).

The expression can also be effected in certain mammalian cell systems. This is effected either with episomal vectors as transient expression, preferably in COS cells (generated by infection of "African green monkey kidney CV1" cells) (Oprian et al. (1987) *Proc Natl. Acad. Sci.* USA 84, 8874 ff.) or HEK cells ("human embryonic kidney cells", e.g. HEK293 cells, Reeves et al. (1996) *Proc. Natl. Acad. Sci. USA* 84, 11487 ff.) or BHK-cells ("baby hamster kidney cells"), or in the form of stable expression (by integration into the genome) in CHO cells ("Chinese hamster ovary cells"), myeloma cells or MDCK cells ("Madine-Darby canine kidney cells") (Review in: Makrides S C (1999) Prot. Expr. Purif. 17, 183-202) or in Sf9 insect cells infected with baculoviruses (Jansen et al. (1988) *Mol Biol. Rep.* 13, 65 ff.).

To ensure or optimise expression, the coding DNA can also be suitably modified, for example by coupling with suitable regulatory sequences and/or by matching of the coding DNA sequence to the preferred codon usage of the chosen expression system.

DESCRIPTION OF DIAGRAMS

FIG. 1

FIG. 1A: Amino acid sequence of Channelopsin1 (Chop1) SEQ ID NO: 1 (AF385748).

FIG. 1B: Amino acid sequence of Channelopsin2 (Chop2) SEQ ID NO: 2 9AF461397).

FIG. 1C: Amino acid sequence of bacterioopsin (Bop) from *Halobacterium salinarium* (BR) (SEQ ID NO:3). The leader sequence, which is cleaved off in vivo and for historical reasons is not counted in the numbering of the amino acids, is indicated in small letters. The amino acids essential for proton conduction are shown in bold letters.

FIG. 1D: Comparison of the amino acid sequences of CHOP-1 (SEQ ID NO: 1 and CHOP-2 (SEQ ID NO: 2) from *Chlamydomonas reinhardtii* with that of bacteriorhodopsin from *Halobacterium salinarum* (SEQ ID NO; 3). Amino acids, which are known to interact directly with retinal in BR (Lucke et al. (1999) Science 286, 255-260 and literature cited therein) are indicated by asterisks. Amino acid positions which are the same in at least two sequences are backed in light grey. Amino acids which contribute to the H.sup.+-conducting network in BR and the amino acids corresponding to these in the other opsins are white against a black background. For the His 173 of CHOP-1, it was shown in the context of the invention that it is involved in the proton conduction. # indicates the position of the retinal-binding lysine. The underlined amino acid indicate the 7 transmembrane helices of the core protein.

FIG. 1E: Amino acid sequence of the CHOP-2 core protein mutant CHOP2-315/-H134R) (SEQ ID NO:4), in which histidine at position 134 is replaced by arginine.

FIG. 2 Photocurrents which were recorded during the irradiation of oocytes with green or red light (500±25 nm and 700±25 nm respectively, $10^{22}$ photons, $M^{-2} s^{-1}$). holding potential ($V_h$)=−100 mV, light pulse indicated by the bar.

Bath solution=96 mM NaCl, 5 mM KCl, 2 mM $CaCl_2$, 1 mM $MgCl_2$, 5 mM MOPS, pH 7.5. A) An oocyte which was not injected with CHOP-1 RNA, irradiated with green light B) a CHOP-1 oocyte, irradiated with green light; C) the same oocyte as in B), irradiated with red light.

FIG. 3 Dependence of the light-induced inward current on the ion conditions and the potential.

a: Results with one (of five) characteristic CHOP-1 oocytes, shown in order of measurement (about 150 sec interval), $V_h$=−100 mV, green light as in FIG. 2. The solutions are buffered with 5 mM MOPS (pH 7.5) or MES (pH 6) or citrate (pH 5 and 4). Concentration in mM:

| 1: | 100 NaCl, 2 $CaCl_2$, pH 7.5 | 2: | 100 NaCl, 2 $CaCl_2$, pH 6.0 (reference) |
|---|---|---|---|
| 3: | 100 Na aspartate, 2 $CaCl_2$, pH 6.0 | 4: | 100 NMG-Cl, 2 $CaCl_2$, pH 6.0 |
| 5: | as in 2 | 6: | 100 NaCl, 2 EGTA, 2 $MgCl_2$, pH 6.0 |
| 7: | 200 sorbitol, 5 EGTA, pH 5.0 | 8: | 200 sorbitol, 5 EGTA, pH 4.0 | b: Current-voltage ratios of the photocurrents of FIG. 3a, see above for concentrations.

Figure 4:
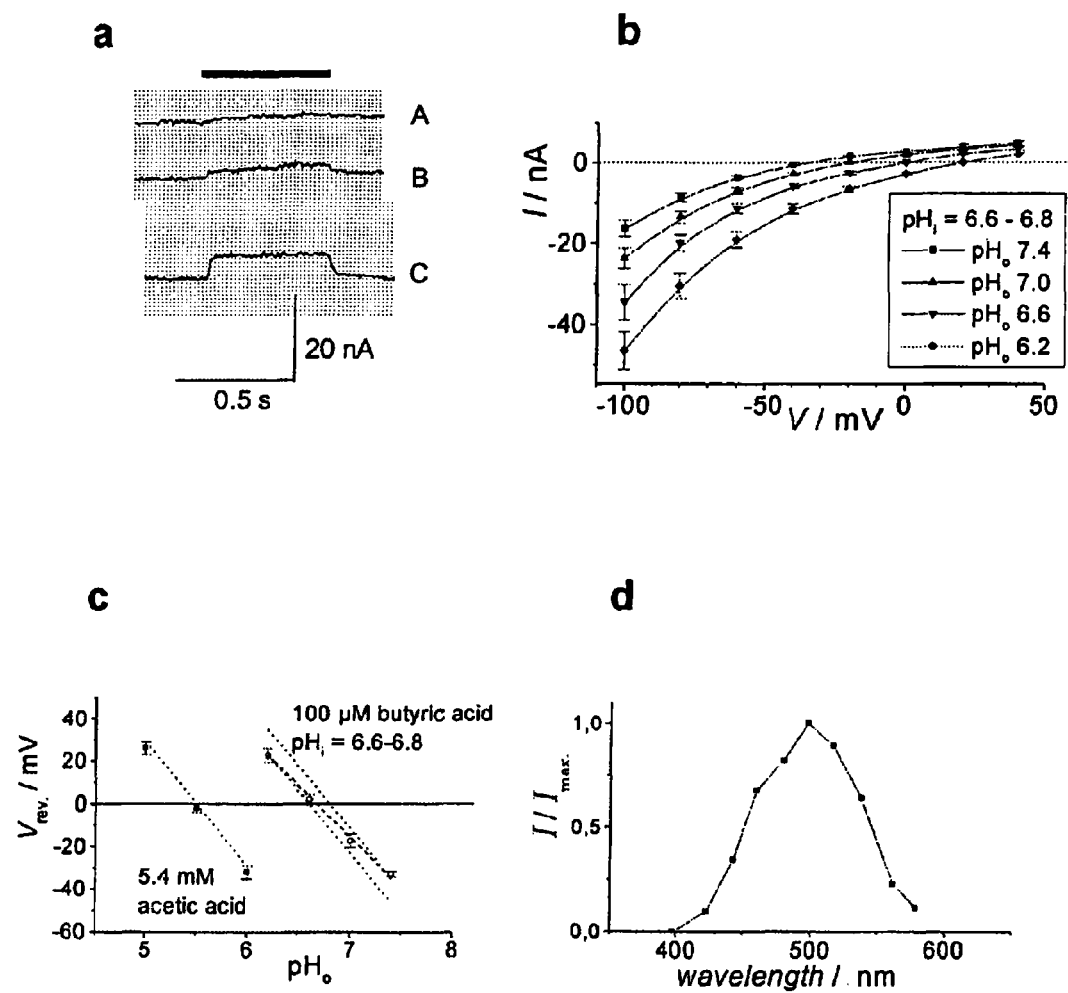

FIG. 4 Photocurrents which were recorded with variation of the external and internal pH value, and their dependence on the wavelength a: Photocurrent at $V_h$=+40 mV. Results from one (of five) characteristic CHOP-1 oocytes in a bath solution of NaCl (100 mM, Track A: red light; Track B: green light; $10^{22}$ photons $m^{-2} s^{-1}$) or sodium butyrate (40 mM, +60 mM NaCl, Track C: green light) of pH 7.4 b: Current-voltage ratios of photocurrents in different bath solutions, which always contained 100 μM undissociated butyric acid:

■, 60 mM NaCl+40 mM Na butyrate, pH 7.4; ▲, 84 mM NaCl+16 mM Na butyrate, pH 7.0; ▼, 93.6 mM NaCl+6.4 mM Na butyrate, pH 6.6; ♦, 97.4 mM NaCl+2.6 mM Na butyrate, pH 6.2;

c: pH dependence of reversal potentials from b. The dotted lines show the theoretical relationship for a constant $pH_i$ of 6.6 or 6.8 and −58 mV/pH. The dashed line shows the expected relationship for a gradient of −48 mV/pH difference and $pH_i$=6.8 at $pH_o$=7.4. The gradient of −48 mV/pH corresponds to a slowly decreasing $pH_i$ (by 0.17 units per $pH_o$ decrease of one unit). ■, pH dependence of reversal potentials from experiments with 5.4 mM of undissociated acetic acid (n=3). The dotted line shows the theoretical relationship for a constant $pH_i$ of 5.5 and −58 mV/pH.

d: Wavelength dependence of the light-induced inward flow at $pH_o$ 5.5 and −40 mV. The photocurrents were standardised for an equal photon flow.

FIG. 5 Photocurrents which were recorded on illumination (wavelength 450±25 nm) of CHOP2-315 expressing oocytes in Ringer's solution (110 mM NaCl, 5 mM KCl, 2 mM $CaCl_2$, 1 mM $MgCl_2$, 5 mM MOPS, pH 7.6) at +40 mV and −80 mV.

FIG. 6 Magnitude of the light-induced equilibrium inflow at −100 mV, pH 9, for 115 mM Li, Na, Cs, TMA, TEA or NMG and for 80 mM $Mg^{2+}$, $Ca^{2+}$, $Sr^{2+}$ or $Ba^{2+}$ (identical for both modifications CHOP2 and CHOP2-315)

FIG. 7 Depolarisation of an oocyte plasma membrane which expresses CHOP2-315, due to a light flash of 200 msecs The following examples illustrate the present invention, without however limiting the invention to these

EXAMPLE I

Amplification of CHOP-1 DNA and Expression of Functional CHOP-1 Photoreceptors in *Xenopus laevis*

A full-length CHOP-1 DNA, coding for the amino acids 1-712, and two shorter CHOP-1 DNAs, respectively coding for the amino acids 1-346 and 1-517 of CHOP-1, were amplified from a full-length cDNA matrix by PCR using a polymerase with correction function (pfu, Promega) and two start oligonucleotides (primers), which contained BamHI and HindIII restriction sites. The products were inserted into the vector pGEMHE (Liman et al., *Neuron* 9, 861-71 (1992)) and cloned in *E. coli*. After checking of the sequences, the CHOP-1 DNAs were transcribed in vitro (Ambion) and 20 to 30 ng cRNA injected into oocytes from *Xenopus laevis*, as already described for bacteriorhodopsin (Nagel et al., FEBS Letters, 377, 263-266 (1995). The oocytes which expressed the CHOP-1 protein were incubated for two to five days with an all-trans retinal (1 µM) in Ringer's solution.

EXAMPLE II

Characterisation of the CHOP-1 Photoreceptor

For the investigation of the supposed ion transport function, the CHOP-1-expressing oocytes were subjected to various experiments using a two-electrode voltage clamp technique which had already been used for bacteriorhodopsin (Nagel et al. FEBS Letters, 377, 263-266 (1995); Nagel et al., *Biophysical Journal* 74, 403-412 (1998)). Green light, but not red light, induced inward-directed currents in oocytes which expressed one of the CHOP-1 RNAs (FIG. 2). The occurrence of photocurrents even with the shorter CHOP-1 RNAs demonstrated that a large part of the carboxy terminal region of CHOP-1 is not necessary for this function. At pH 6 and a transmembrane potential between −100 and +40 mV the photocurrents were always inward-directed (FIG. 3b). The replacement of chloride by aspartate in the solution had no detectable effect on the amplitude of the photocurrent (FIG. 3a) or its current-voltage ratio (FIG. 3b), a result which ruled out $Cl^-$ as the ion transported. The replacement of sodium by N-methyl-D-glucamine (or of NaCl by sorbitol, data not shown) resulted in a similar inward-directed current (FIG. 3a) with no change in the current-voltage ratio (FIG. 3b), which indicates that $Na^+$ is not transported by CHOP-1. Likewise, the replacement of $Ca^{2+}$ by $Mg^{2+}$ gave no change in the photocurrents, a result which showed that $Ca^{2+}$ was also not the ion transported (FIG. 3a,b).

Figure 3A:
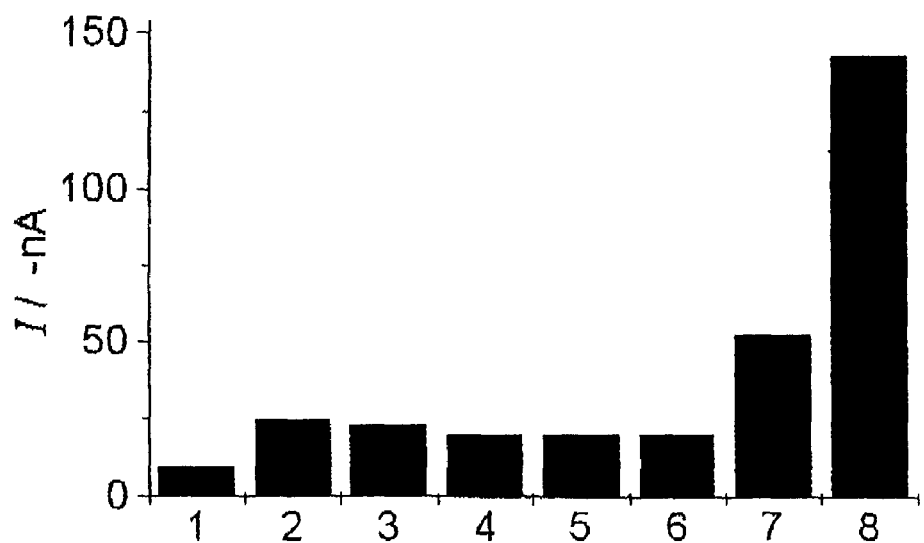
Figure 3B:
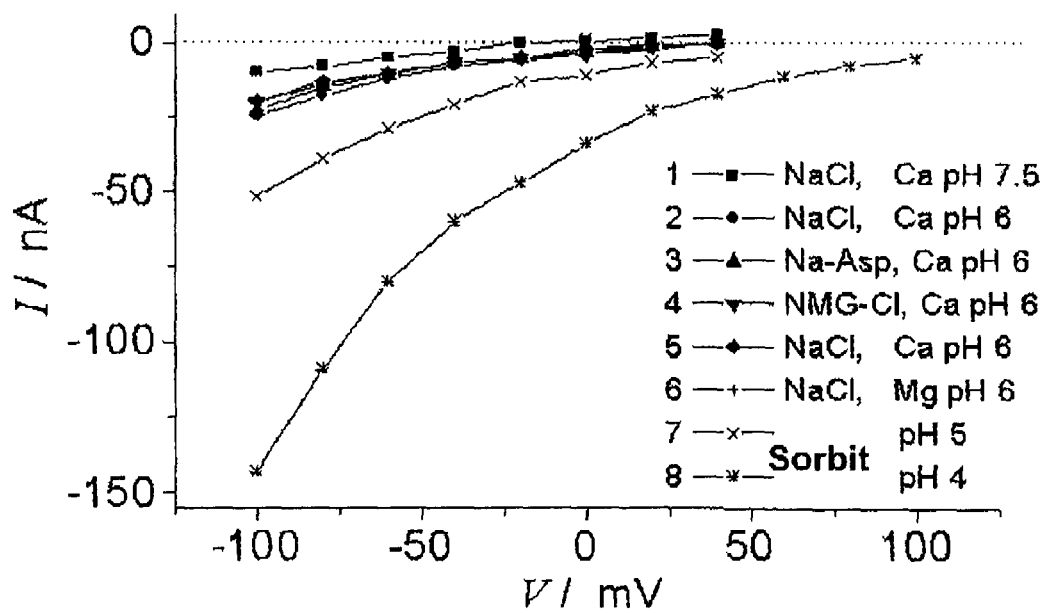

On the other hand, an increase in the proton concentration in the bath solution, $[H^+]_o$, to pH values of 5 and 4 at potentials between −100 and +40 mV resulted in marked increases in the inward-directed photocurrents (FIG. 3a,b).

The results obtained so far thus point to $H^+$ ions as the charge carriers in the light-induced currents. On account of the sequence homologies between the CHOP-1 protein and the proton pump bacteriorhodopsin mentioned at the outset, it was at first obvious to suppose that the CHOP-1 protein was also a component of an active ion transport system, namely a proton pump such as bacteriorhodopsin.

However, while bacteriorhodopsin always transports protons outwards at all membrane potentials tested from −60 mV to +40 mV (see for example Nagel et al., *Biophysical Journal* 74, 403-412 (1998)) even against an existing pH gradient, the transport direction of the CHOP-1 system was dependent on the pH gradient present across the membrane and the membrane potential (FIG. 4a,b,c). The measured reversal potentials at different initial pH gradients (FIG. 4b,c) clearly confirm that the light-induced currents are of a purely passive nature. From the high photocurrents observed, it can be concluded that the proton transport does not proceed only via facilitated diffusion of the protons through the membrane, but rather that the CHOP protein is a proton channel.

The dependence of the light-induced inward-directed photocurrent at pH 5.5 and −40 mV on the wavelength of the light is shown in FIG. 4d. The maximum in the vicinity of 500 nm corresponds to the action spectra for photoreceptor currents, for phototaxia and photoshock reactions of intact *C. reinhardtii* cells.

EXAMPLE III

Amplification of CHOP-2 DNAs and Expression of Functional CHOP-2 Photoreceptors in *Xenopus laevis*

A full-length CHOP-2 DNA, coding for the amino acids 1-737, and a C-terminally truncated CHOP-2 DNA, coding for the amino acids 1-315 of CHOP-2, were amplified from a full-length cDNA matrix by PCR using a polymerase with correction function (pfu, Promega) and primers which contained BamHI and HindIII restriction sites. The products were inserted into the vector pGEMHE (Liman et al., *Neuron* 9, 861-71 (1992)) and cloned in *E. coli*. After checking of the sequences, the CHOP-2 DNAs were transcribed in vitro (Ambion) and 20 to 30 ng cRNA injected into oocytes of *Xenopus laevis*, as already described for bacteriorhodopsin (Nagel et al., FEBS Letters, 377, 263-266 (1995). The oocytes which expressed the CHOP-2 protein were incubated for two to five days with an all-trans-Retinal (1 µM) in Ringer's solution.

EXAMPLE IV

Characterisation of the CHOP-2 Photoreceptors

For the investigation of the ion transport function, the CHOP-2-expressing oocytes, which had been incubated with retinal in Ringer's solution for the formation of the ChR2 (Channelrhodopsin2) ion channel were subjected to various experiments (FIGS. 5-7) using similar two-electrode voltage clamp techniques, such as had already been used for CHOP-1 and ChR1.

FIG. 5 shows that the light-induced photocurrent on irradiation with steady light (wavelength 450±25 nm; corresponds roughly to the maximum of the action spectrum) declines to an equilibrium level. This means that the ChR2 ion channel is desensitised by steady light of this wavelength, possibly by inactivation of a part of the ChR2 molecules.

FIG. 6 demonstrates that the ion channel formed with CHOP-2, in contrast to the ion channel formed with CHOP-1, is a non-selective cation channel, which as well as protons also allows various mono and divalent cations to pass. Here the conductivity for the monovalent cations studied decreases in the order $Li^+>Na^+>K^+>Cs^+>>TMA^+$ (tetramethylammonium)=$TEA^+$ (tetraethylammonium), i.e. with increasing ionic radius. With divalent cations, the conductivity also decreases with increasing ionic radius. Here, however, $Mg^{2+}$ is the exception. ChR2 is not permeable to $Mg^{2+}$, probably on account of the high hydration energy of this ion (Diebler et al., Pure Appl. Chem. 20, p. 93, 1969). At the same time, the respective photocurrents for the ion channel formed with full-length CHOP-2 do not differ from the corresponding photocurrents for the ion channel which contains the CHOP-2 fragment with the amino terminal amino acids 1-315, which allows the conclusion that the cation conductivity is determined by the amino terminal part of the CHOP-2 protein, which contains the seven presumed transmembrane domains.

The invention claimed is:

1. A method for increasing or decreasing ion conductivity of a membrane, the method comprising
inserting one or more directly light-controlled ion channels into a membrane,
wherein the one or more directly light-controlled ion channels is a biological photoreceptor, and wherein the one or more directly light-controlled ion channels comprises:
(a) SEQ ID NO:2,
(b) amino acids 1 to 315 of SEQ ID NO:2, or
(c) an amino acid sequence having at least five transmembrane helices, wherein said amino acid sequence comprises one or more conservative amino acid changes relative to the corresponding region of SEQ ID NO:2 provided that the amino acid sequence has at least 52.7% identity to SEQ ID NO:2, and comprises aspartic acid at position 253 of SEQ ID NO:2, lysine at position 257 of SEQ ID NO:2, tryptophan at position 260 of SEQ ID NO:2, glutamic acid at position 123 of SEQ ID NO:2, and histidine or arginine at position 134 of SEQ ID NO:2; and
a light-sensitive retinal or retinal derivative.

2. The method of claim 1, wherein the directly light-controlled ion channel is a transport system for protons, sodium, or calcium.

3. The method of claim 1, wherein the one or more directly light-controlled ion channels comprises (c) and wherein the position 134 of SEQ ID NO: 2 is arginine.

4. The method of claim 1, wherein retinal is bound to the one or more directly light-controlled ion channels.

5. The method of claim 1, wherein a retinal derivative is bound to the one or more directly light-controlled ion channels.

6. The method of claim 5, wherein the retinal derivative is selected from the group consisting of 3,4-dehydroretinal, 13-ethylretinal, 9-dm-retinal, 3-hydroxyretinal, 4-hydroxyretinal, naphthylretinal; 3,7,11-trimethyl-dodeca-2,4,6,8,10-pentaenal; 3,7-dimethyl-deca-2,4,6,8-tetraenal; 3,7-dimethyl-octa-2,4,6-trienal; and 6-7 rotation-blocked retinals, 8-9 rotation-blocked retinals, and 10-11 rotation-blocked retinals.

7. The method of claim 1, wherein the proton, sodium, or calcium conductivity of a membrane is increased.

8. The method of claim 1, wherein the proton, sodium, or calcium conductivity of a membrane is decreased.

9. The method of claim 1, wherein the membrane potential of a cell membrane is increased.

10. The method of claim 1, wherein the membrane potential of a cell membrane is decreased.

11. The method of claim 1, wherein the membrane is a cell membrane of a yeast.

12. The method of claim 1, wherein the yeast is *Saccharomyces cerevisiae, Schizosaccharomyces pombe*, or *Pichia pastoris*.

13. The method of claim 1, wherein the membrane is a cell membrane of a mammalian cell or an insect cell.

14. The method of claim 13, wherein the membrane is a cell membrane of a mammalian cell and is a COS cell, a BHK cell, a HEK293 cell, a CHO cell, a myeloma cell, an MDCK cell, or a neuron.

15. The method of claim 13, wherein the membrane is a cell membrane of an insect cell which is a baculovirus-infected sf9 cell.

16. The method of claim 5, wherein the concentration gradient of ions across the membrane is raised or lowered.

17. The method of claim 16, wherein the concentration gradient of protons, sodium, or calcium across the membrane is raised or lowered.

18. The method of claim 5, wherein a light-induced membrane depolarization is realized by lowering the ion conductivity of the membrane by activating the one or more directly light-controlled ion channels by exposure to light.

19. The method of claim 1, wherein the one or more directly light-controlled ion channels comprises (a).

20. The method of claim 1, wherein the one or more directly light-controlled ion channels comprises (b).

21. The method of claim 1, wherein the one or more directly light-controlled ion channels comprises (c).

\* \* \* \* \*